United States Patent [19]

Kaufman

[11] 4,451,563

[45] May 29, 1984

[54] METHOD FOR INCREASING THE SENSITIVITY OF ASSAYS

[76] Inventor: Richard A. Kaufman, 812 Stonegate La., Stanhope, N.J. 07874

[21] Appl. No.: 297,483

[22] Filed: Aug. 28, 1981

[51] Int. Cl.$^3$ .................. C12Q 1/34; C12Q 1/38; C12Q 1/40; C12Q 1/42; C12Q 1/44; C12Q 1/54

[52] U.S. Cl. .................. 435/21; 424/7.1; 435/14; 435/18; 435/19; 435/20; 435/22; 435/23; 435/24; 436/93; 436/94; 436/95; 436/164

[58] Field of Search .................. 23/230 B; 252/408; 424/7; 435/22, 14, 18, 19, 20, 21, 22, 23, 24; 436/66, 93, 94, 95, 96–99, 125

[56] References Cited

U.S. PATENT DOCUMENTS

| | | | |
|---|---|---|---|
| 4,102,747 | 7/1978 | Driscoll et al. | 435/22 |
| 4,121,975 | 10/1978 | Ullman et al. | 23/230 B |
| 4,225,672 | 9/1980 | Hall | 435/22 |
| 4,233,403 | 11/1980 | Menson et al. | 435/22 |
| 4,252,783 | 2/1981 | Kam et al. | 23/230 B |
| 4,294,923 | 10/1981 | Smith et al. | 435/23 |
| 4,338,433 | 7/1982 | Matsumura et al. | 536/46 |
| 4,376,197 | 3/1983 | Wallenfels | 435/22 |

FOREIGN PATENT DOCUMENTS

| | | | |
|---|---|---|---|
| 3000292 | 7/1981 | Fed. Rep. of Germany | 435/22 |
| 54-43791 | 4/1979 | Japan | 435/28 |
| 57-102198 | 6/1982 | Japan | 435/24 |
| WO82/01564 | 5/1982 | PCT Int'l Appl. | 435/24 |
| 2088052 | 6/1982 | United Kingdom | 435/22 |

OTHER PUBLICATIONS

Kojima, M., et al., J. C. S. Perkin I, pp. 1647–1651 (1981).
Breslow, R., et al., JACS, vol. 102, No. 2, pp. 762–770 (1980).
Harhta, K., et al., Bull. Chem. Soc. Jap., vol. 51, No. 6, pp. 1627–1634 (1978).
Bergeron, R. J., et al., JACS, vol. 99, No. 15, pp. 5146–5151 (1977).
C. A., vol. 94, 60560h (Mar. 2, 1981).
C. A., vol. 95, 255029q (Jul. 20, 1981).
Gelb, R. I., et al., Anal. Biochem., vol. 103, pp. 362–368 (1980).
Gelb, R. I., et al., JACS, vol. 101, No. 7, pp. 1869–1874 (1979).
Bergeron, R. J., et al., JACS, vol. 100, No. 9, pp. 2878–2883 (1978).

*Primary Examiner*—Teddy S. Gron
*Attorney, Agent, or Firm*—John H. Faro

[57] ABSTRACT

This invention relates to diagnostic reagents and a method for increasing the sensitivity of chemical and enzymatic analysis. In particular, it relates to an improved reagent and method wherein the sensitivity of the analysis is improved by the addition of a water-soluble inclusion compound.

10 Claims, 5 Drawing Figures

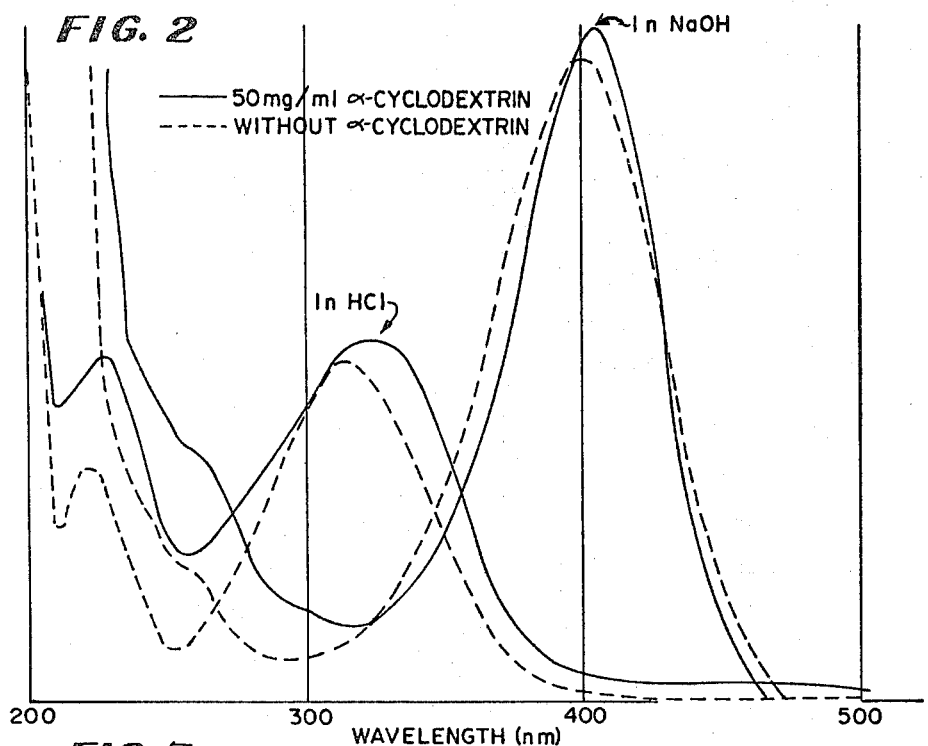
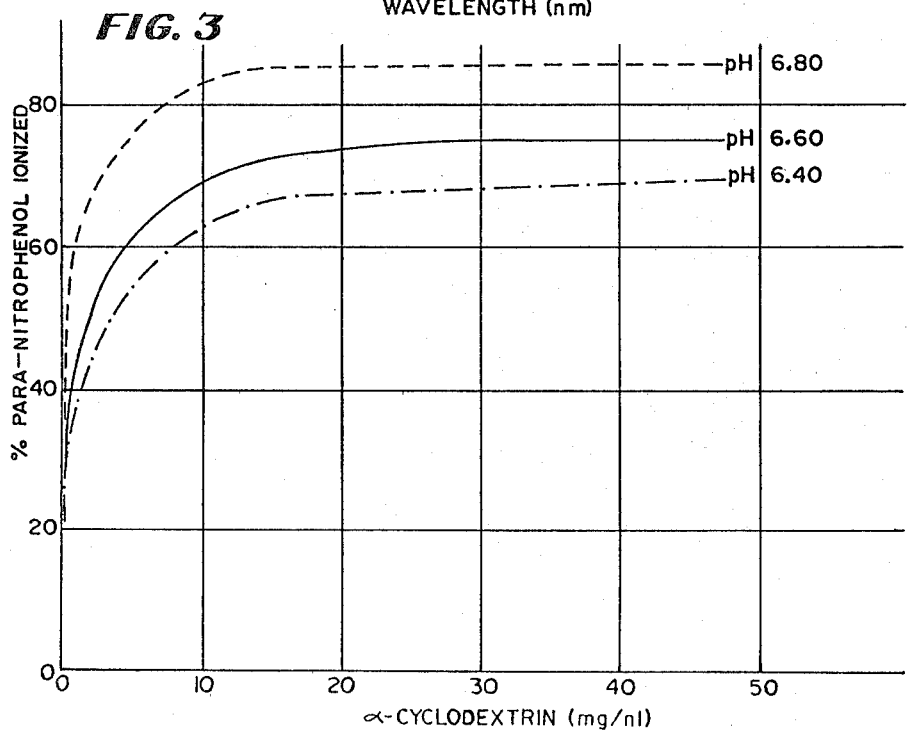

METHOD FOR INCREASING THE SENSITIVITY OF ASSAYS

BACKGROUND OF THE INVENTION

The complete analysis of biological fluids in the clinical chemistry laboratory requires the use of many different techniques to insure that all of the constituents are measured. Some of the techniques, and in particular those techniques used in the analysis of inorganic and organic materials, are not applicable to measuring enzymes, since the enzyme protein usually represents only a small part of the total mass of other proteins. Thus, the specific quantitation of enzymes in biological fluids and other complex enzyme mixtures is conventionally performed by measuring the enzyme's unique biochemical property of catalyzing a specific chemical reaction. When a chemical substrate is transformed by an enzyme, it is possible to correlate the degree of catalytic transformation to the amount of enzyme in the mixture.

The use of diagnostic indicator groups for chemical and enzymatic analysis has facilitated the determination of these constituents in clinical assays. In particular, diagnostic indicator groups have been widely used with substrates for enzymatic analysis since they provide an easily detectable means of monitoring enzyme activity. Diagnostic indicators can be covalently attached to substrates, or complexed with substrates through non-covalent interactions, both of which are disrupted by the action of an enzyme.

Indicators specifically related to the present invention include compounds having readily convertible ionized and unionized forms, such as substituted phenol chromophores. Illustrative of these substituted phenol compounds are para-nitrophenylphosphate and para-nitrophenylmaltoheptaoside which are presently used for the determination of alkaline phosphates and amylase activity, respectively. In both of these assays, the nitrophenol group is cleaved from its respective substrate by hydrolytic action of the enzyme producing an indicator having both an ionized and unionized form at or about neutral pH. Since the $pK_a$ of the phenolic group is about 7, approximately equal portions of the ionized and unionized forms are present at neutral pH where most enzymatic assays are conducted. However, since the unionized form of the indicator absorbs maximally at about 320 nm and the ionized form absorbs maximally at about 400 nm, only a portion of the liberated indicator is detected when a single wavelength of the spectrum is monitored. An additional limitation is that the unionized nitrophenol compound in this example does not absorb in the visible wavelength range of the spectrum and thus cannot be directly detected colorimetrically.

The alkaline phosphatase assay is performed at alkaline pH where the liberated phenol is converted to the para-nitrophenoxide ion having a quinoid structure. The progress of the reaction is monitored at a wavelength of 405 nm due to the formation of a yellow color associated with this quinoid compound. In the kinetic assay, the rate of hydrolysis of para-nitrophenol by alkaline phosphatase enzyme can adequately be monitored at the pH optimum of the reaction, namely pH 10.3, since the majority of the phenoxide is in the quinoid form. In the end-point procedure, the reaction is permitted to proceed for a predetermined time at the pH having maximal enzyme activity, and is then stopped by adding NaOH to raise the pH to 11.5 to 12.0. The increase in pH inactivates the enzyme and converts all of the phenoxide to the colored quinoid form.

The kinetic analysis of other enzymatic assays utilizing substituted phenol substrates is generally conducted at lower pH values than alkaline phosphatase since their maximal enzymatic activity occurs at about neutral pH, slightly above, or below. In these kinetic assays, both the ionized and unionized forms of the liberated phenol indicator are present in approximately equal proportions, thus reducing the amount of detectable indicator in the assay mixture. The analyst must either sacrifice sensitivity in the kinetic assay by performing the assay at a pH well above that having maximal enzymatic activity, or conduct the end-point procedure by terminating the reaction with alkali. Heretofore, kinetic enzyme assays or chemical assays conducted at or about neutral pH and employing ionizable chromophores and in particular nitrophenol as diagnostic indicator groups were usually monitored at about 390-420 nm, and thus a considerable amount of the diagnostic indicator remained undetected. The improved reagent and method of the present invention overcomes these difficulties and provides an increased sensitivity for chemical and enzymatic assays.

SUMMARY OF THE INVENTION

In accordance with the present invention, we have discovered an improved diagnostic reagent for chemical and enzymatic assays, wherein said reagent contains a diagnostic indicator having convertible chemical or physical states, wherein the improvement comprises increasing the sensitivity of said assay by the addition of a water-soluble inclusion compound such as cyclodextrin.

DETAILED DESCRIPTION OF THE INVENTION

The invention described herein employs a water-soluble inclusion compound such as cyclodextrin in chemical and enzymatic assays. An improved reagent and method have been developed which substantially increase the sensitivities of assays using diagnostic indicators such as substituted phenols and other chromophores which have convertible chemical and physical states. In accordance with one embodiment of the present invention, incorporating cyclodextrin into a reagent wherein one of the convertible forms of the indicator preferentially interacts with the cyclodextrin to form an inclusion complex, causes a change in the degree of ionization of the indicator. This results in a substantial increase in the detection of one of the convertible forms at the expense of the other, permitting the kinetic analysis of enzymes to be conducted with greater sensitivity at the pH of maximum enzyme activity. Specific examples of the use of the present invention include kinetic enzyme assays of amylase, alpha-glucosidase, and proteases in biological fluids which use nitrophenol indicators as part of their substrate.

In accordance with one embodiment of the present invention, the effect of the cyclodextrin addition to the reagent is to cause a substantial increase in the absorbance of para-nitrophenoxide ion at wavelengths between 390 and 420 nm with a concomitant decrease in absorbance of the unionized para-nitrophenol at wavelengths between 300 and 320 nm. Since the cyclodextrin addition lowers the $pK_a$ of the para-nitrophenol ⇌ para-nitrophenoxide equilibrium, the pH of an amylase reagent, for example, can be reduced from about 7.3 to about 6.6, which is the optimum pH for the determination of amylase activity found in serum and urine using para-nitrophenyl-alpha-D-maltoheptaoside as substrate. This results in a considerable increase in the sensitivity of the measured amylase activity.

The formation constants of alpha-cyclodextrin with para-nitrophenol and para-nitrophenoxide ion have been determined using various techniques [Gelb et al., *Analytical Biochemistry*, 103, 362–368 (1980)]. At 30° C. the respective log of the formation constants for an alpha-cyclodextrin para-nitrophenol complex and the alpha-cyclodextrin para-nitrophenoxide ion complex are 2.251 and 3.209, respectively. Thus, due to a much greater stability of the alpha-cyclodextrin para-nitrophenoxide ion complex, the equilibrium for the following reaction is shifted to a significantly increased proportion of para-nitrophenoxide ion:

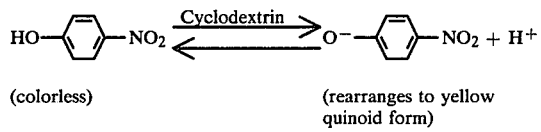

(colorless)        (rearranges to yellow quinoid form)

and consequently to an increase in absorbance at about 390–420 nm.

In accordance with one embodiment of the present invention, the interaction of cyclodextrin with nitrophenol and nitrophenoxide ion produces a hypochromic shift in the wavelength range corresponding to the absorbance maxima of both these compounds. We have found that these hypochromic shifts in the absorbance maxima are advantageous in enzyme assays using substituted indicator groups as substrates. Substrates to which a nitrophenol group is attached and other interfering substances in serum such as bilirubin and hemoglobin are known in some instances to have an appreciable absorbance at 398 nm, which is the wavelength for the absorbance maxima for the nitrophenoxide ion. The hypochromic wavelength shift in the absorbance maxima of the p-nitrophenolate anion may be advantageous in enzyme assays using substrates containing the p-nitrophenol chromophore. Many of these substrates at the concentrations normally used in enzyme assays have an appreciable absorbance at 398 nm.

An example of an assay using a substrate containing the p-nitrophenol chromophore which has appreciable absorbance at 400 nm is the alkaline phosphatase substrate, p-nitrophenyl phosphate. In this assay, activity is determined by quantitating the amount of substrate hydrolyzed to p-nitrophenol during a given time interval. At the concentrations of the substrate normally used in this assay the absorbance at 400 nm is substantial. To overcome this interference a wavelength of 405 nm is typically used to monitor the rate of production of p-nitrophenol and hence the alkaline phosphatase activity. Incorporation of cyclodextrin into the assay reagent shifts the absorbance maxima of the phenoxide form of the indicator to about 405–407 nm such that interference due to the substrate absorbance can be substantially reduced or eliminated without sacrificing sensitivity of the absorbance measurement as presently done.

In accordance with the present invention, the cyclodextrins belong to a class of macrocyclic nonreducing D-glucosyl polymers containing six or more residues bonded by $\alpha$-(1→4) links. Cyclodextrins are referred to as cycloglucans, Schardinger dextrins, and sometimes simply as dextrins, although this latter term can be confused with other compounds. Two systems of nomenclature are in current use. The first of these indicates the number of residues in the cyclic polymer by prefixing a Greek letter to the series name. Since the smallest known cycloamylose is a hexamer, it is assigned the prefix alpha. The cyclic heptaose, octaose, etc. are referred to respectively as beta, gamma, etc. dextrins. In the alternate system, the homologs, are designated by the names of cyclohexaamylose, cycloheptaamylose, and cyclooctaamylose, the Greek prefix corresponding to the degree of polymerization. In shape, these molecules approximate a torus and are capable of forming inclusion compounds in solution.

In accordance with one embodiment of the present invention, cyclodextrins in general can be used to increase the sensitivity of chemical and enzymatic assays. Preferably, alpha- and beta-cyclodextrins are used. We have found that alpha-cyclodextrin is most preferred in accordance with the present invention. The effective concentration of alpha-cyclodextrin necessary to give increased sensitivity is from about 0.1 to about 100 mg/ml.

The effective upper limit of cyclodextrin concentration, however, may be limited by the solubility in the buffer used and can be varied according to specific reaction conditions. In accordance with the present invention, the preferred concentration of cyclodextrin is from about 0.1 to about 100 mg/ml. The most preferred concentration in accordance with the present invention is from about 5 to about 50 mg/ml.

BRIEF DESCRIPTION OF THE DRAWINGS

FIG. 2 illustrates the hypochromic shift in absorbance wavelength of p-nitrophenol produced by alpha- and beta-cyclodextrins.

FIG. 3 is a plot of alpha-cyclodextrin concentration versus percent ionized p-nitrophenol.

In accordance with the present invention, diagnostic indicator groups are compounds which can become covalently attached to or complexed with substrates, and are liberated or altered by enzymatic action to provide an indication that some change has taken place. In accordane with one embodiment the present invention, diagnostic indicator groups having convertible chemical or physical states are liberated from substrates by enzymatic hydrolysis. The conversion from a first convertible state to a second convertible state by preferential interaction of the latter with cyclodextrins permits the detection and analysis of only one form of the compound rather than two or more. Examples of convertible chemical or physical states are the ionized and unionized forms of a compound in chemical equilibrium. In accordance with the present invention, preferred indicator groups are those compounds which exhibit a detectable change in $pK_a$, and preferably a change of about $\pm 0.25$ $pK_a$ units when associated with the inclusion compound. In accordance with the present invention, substituted phenolic compounds and barbiturates are more preferred convertible diagnostic indicators. The most preferred indicators in accordance with the present invention are nitrophenols such as para- and meta-nitrophenols, which are examples of chromophores having visually detectable and visually undetectable ionizable forms.

In accordance with the present invention, illustrative examples of diagnostic indicator groups having readily convertible states and appropriate $pK_a$ characteristics are listed in Table I.

TABLE I

| | |
|---|---|
| Benzoic Acid | Barbituric Acid |
| m-Hydroxybenzoic acid | Phenobarbital |
| p-Hydroxybenzoic acid | Mephobarbital |
| m-methoxybenzoic acid | Amobarbital |
| p-Nitrobenzoic acid | Cyclobarbital |
| p-Fluorobenzoic acid | Pentobarbital |
| o-Methoxybenzoic acid | Metharbital |
| Salicylic acid | Barbital |
| Cinnamic acid | 4-Biphenylcarboxylate |
| Gallic acid | m-Methoxycinnamic acid |
| o-Hydroxycinnamic acid | p-Methoxycinnamic acid |
| m-Hydroxycinnamic acid | m-Nitrophenol |
| p-Hydroxycinnamic acid | p-Nitrophenol |
| o-Methoxycinnamic acid | 2-Napthol |

In accordance with the present invention, illustrative examples of enzymes and their respective substrates are listed in Table II below:

TABLE II

| Enzyme | Substrate |
|---|---|
| alpha amylase | *nitrophenyl oligoglycosides |
| alpha and beta glucosidases | *nitrophenyl glycosides |
| beta-galactosidase | *nitrophenyl galactosides |
| alpha mannosidase | *nitrophenyl mannosides |
| alpha fucosidase | *nitrophenyl fucosides |
| acid phosphatase | *nitrophenyl phosphates |
| alkaline phosphatase | *nitrophenyl phosphates |

*para- and meta-derivatives

The following examples in accordance with the present invention are to be illustrative only and are not intended to be scope limiting.

EXAMPLE 1

Figure 1:
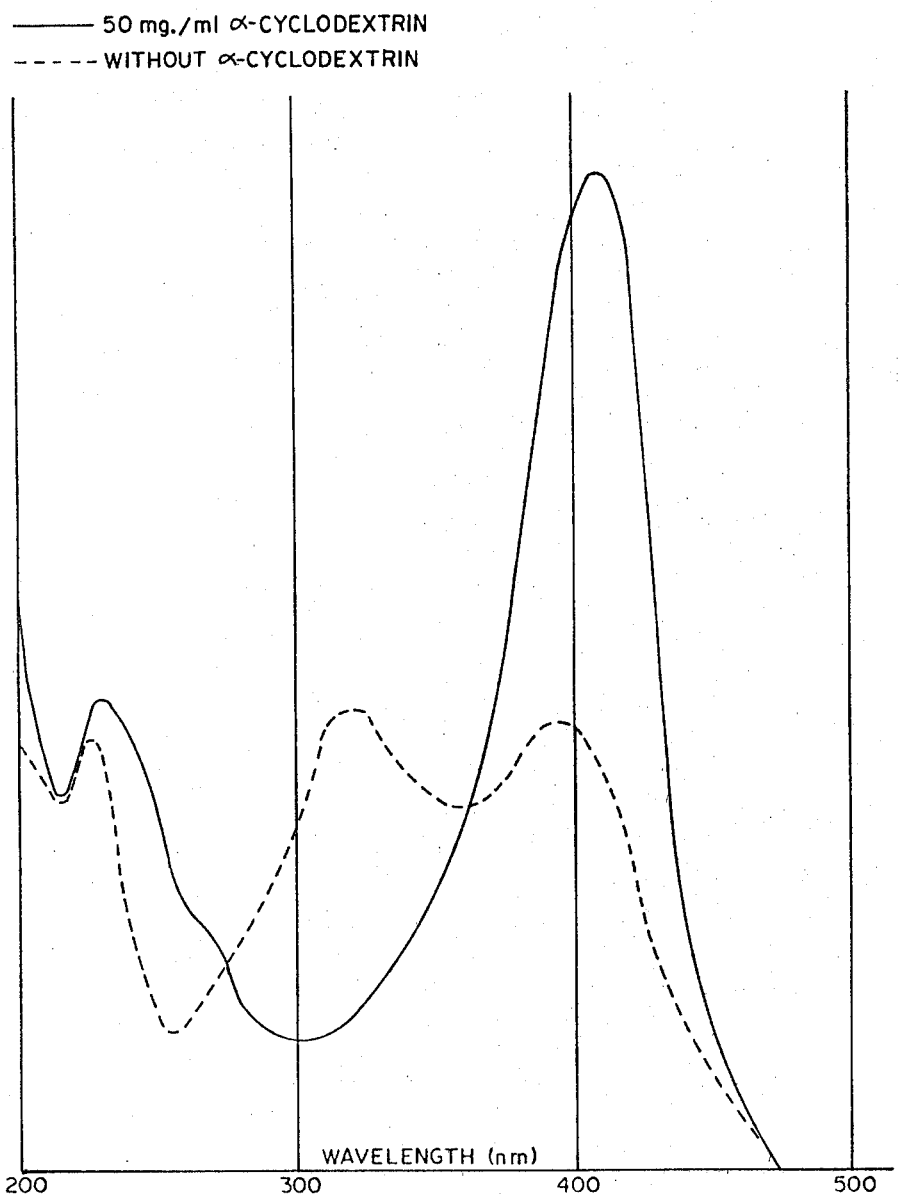
FIG. 1 illustrates the effects of cyclodextrin added to p- and m-nitrophenol.

FIG. 1 illustrates the effects of the cyclodextrin added to para- and meta-nitrophenol solutions wherein the absorbance spectra of para-nitrophenol in 0.10 molar sodium phosphate buffer, pH 6.8 with and without alpha-cyclodextrin in the buffer, is shown. In the absence of alpha-cyclodextrin in the buffer (dotted line), the absorbances at approximately 318 nm and approximately 397 nm, corresponding respectively to the unionized and ionized forms of para-nitrophenol, are approximately equal. When alpha-cyclodextrin is added at a concentration of 50 mg/ml of buffer (solid line) and the spectrum rerun, the absorbance maxima at approximately 318 nm virtually disappears, while the absorbance maxima at approximately 397 nm increases significantly and is shifted to a longer wavelength at about 406 nm. An analogous situation occurs when the same buffer is used with and without beta-cyclodextrin.

EXAMPLE 2

Alpha and beta cyclodextrins produce a hypochromic shift in the wavelengths corresponding to the absorbance maxima of the unionized and ionized forms of para-nitrophenol. These hypochromic shifts are shown in FIG. 2, which are the absorbance spectra of (1) para-nitrophenol in 0.1 mol/liter sodium phosphate buffer, pH 7.00 containing 0.05 mol/liter NaCl which has been diluted with an equal volume of 1.0 mol/liter hydrochloric acid, final pH approximately 1 and (2) para-nitrophenoxide in 0.1 mol/liter sodium phosphate buffer, pH 7.00 containing 0.05 mol/liter NaCl and diluted with an equal volume of 1.0 mol/liter sodium hydroxide, final pH approximately 13. Each of these spectra were determined with (solid line) and without (dotted line) alpha-cyclodextrin in solution. The absorbance spectra shows that the absorbance maxima of the unionized para-nitrophenol is shifted from about 316 nm to 328 nm when alpha-cyclodextrin is added to the solution. A similar hypochromic wavelength shift occurs with the para-nitrophenoxide ion in the presence of alpha-cyclodextrin. In this instance, the absorbance maxima is shifted from about 398 nm to about 406 nm.

EXAMPLE 3

The effective concentration of alpha-cyclodextrin necessary to give increased sensitivity is from about 0.1 to about 100 mg/ml. FIG. 3 is a graph of the percent ionization of para-nitrophenol as a function of the concentration of alpha-cyclodextrin in buffer. Data given for three different pH values indicates a dramatic shift in equilibrium with the addition of cyclodextrin.

Figure 4:
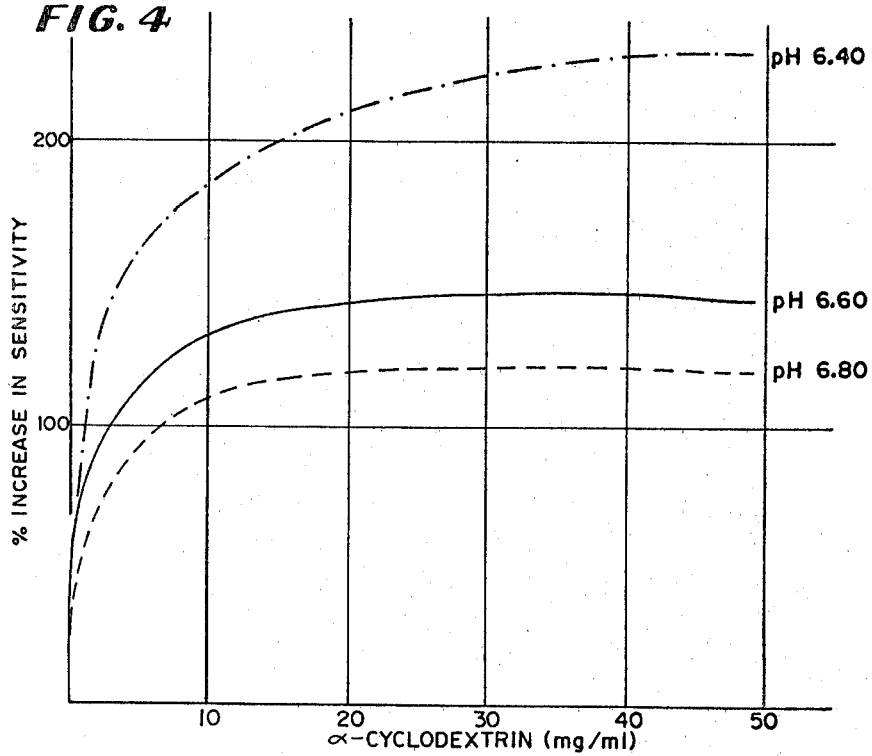
FIG. 4 is percent increase in sensitivity versus alpha-cyclodextrin concentration.

In FIG. 4 is a graph of the same data except that the percent increase in sensitivity (defined as the absorbance at 406 nm with alpha-cyclodextrin in the buffer divided by the absorbance at 398 nm of the same buffer without alpha-cyclodextrin) is plotted as a function of the concentration of alpha-cyclodextrin/ml buffer. Data are given for three different pH values. It is noted that the effect becomes more dramatic the lower the pH. The alpha-cyclodextrin concentration is seen to be effective down to 0.1 mg/ml of cyclodextrin in buffer. The maximum effect is usually seen at about 5–25 mg/ml. Concentrations beyond these and up to 50 mg/ml do not significantly enhance sensitivity. Effective concentrations could conceivably be used up to the solubility limit in the buffer.

EXAMPLE 4

An example of the use of the invention is in the analysis of alpha-amylase activity using the substrate, para-nitrophenyl-alpha-D-maltoheptaoside, in the coupled enzyme assay shown below:

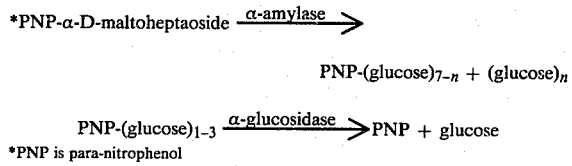

*PNP is para-nitrophenol

In this assay (U.S. Pat. No. 4,102,747), para-nitrophenyl-alpha-D-maltoheptaoside is hydrolized by alpha-amylase into shorter chain PNP-glycosides and oligosaccharides. The shorter chain PNP-glycosides containing from one to three glucose units are then hydrolized by alpha-glucoside to free para-nitrophenol and glucose. Alpha-amylase activity is determined in this assay using a rate or kinetic procedure by measuring the increase in absorbance at 406 nm as a function of time after adding the sample to the assay reagent.

This assay had previously been developed using a reagent having a pH of 7.00. This pH, however, was not the optimum for alpha-amylases found in human serum, but was a pH that gave sufficient sensitivity in the expected normal range using 1/20:sample/reagent volume ratio. For alpha-amylases found in serum, the pH of maximum sensitivity occurs at 7.3, which is significantly different from the pH for maximum amylase activity, namely, about 6.5 when para-nitrophenyl-alpha-D-maltoheptoaside is used as the substrate. This is due to the fact that the increase in the ionization of para-nitrophenol with increasing pH more than offsets the decrease in amylase activity until a pH of about 7.3 is reached. When alpha-cyclodextrin is added to the reagent at a concentration of 10 mg/ml, the pH of maximum sensitivity is changed from 7.3 to 7.0 with, in addition, a substantial increase in sensitivity of about 50%. With the increased sensitivity due to the alpha-cyclodextrin in the reagent, it is now possible to measure alpha-amylase activity found in human serum using an amylase reagent of about pH 6.5 which is about the pH optimum using the para-nitrophenol-alpha-D-maltoheptaoside substrate. Additional advantages of using this pH are that less substrate and less activity of the coupling enzyme, alpha-glucoside, are needed.

Another example of an enzyme assay that has been examined using alpha-cyclodextrin in the reagent is alpha-glucosides. This assay uses the substrate para-nitrophenyl-alpha-D-glucoside which is hydrolized by alpha-glucosidase to give glucose and para-nitrophenol. The enzyme activity is determined using a kinetic rate assay by measuring the change in absorbance permitted at 406 nm from one to five minute interval after adding the sample to the reagent.

EXAMPLE 5

Figure 5:
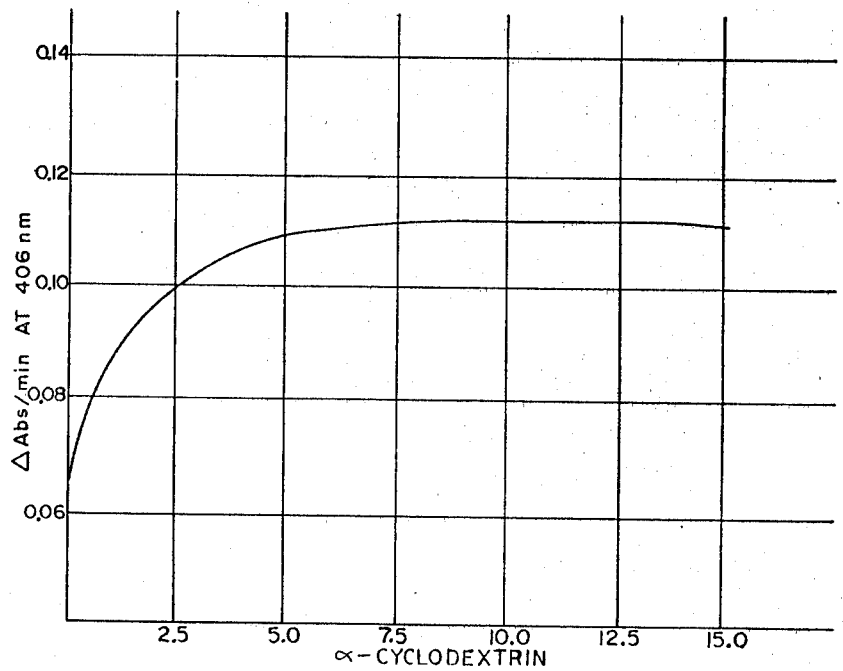
FIG. 5 shows optimum alpha-cyclodextrin concentrations.

The alpha-amylase assay reagent is prepared by adding 13.80 grams of $NaH_2PO_4H_2O$ to about 900 ml deionized or distilled water and 1.46 grams NaCl. After the salts have dissolved, adjust the pH to 6.50 with 1 mol/liter NaOH. Dissolve 2.0 grams of amylase substrate (para-nitrophenyl-alpha-D-maltoheptaoside) in the pH 6.50 buffer. Add 6.0 grams of alpha-cyclodextrin and mix until completely dissolved. The optimal concentration of alpha-cyclodextrin can be determined by optimizing the reagent as shown in FIG. 5. It can be seen that the optimal concentration is from about 2:1 to about 7:1 cyclodextrin to substrate on a weight basis. Add 225,000 units of alpha-glucoside, and mix gently until dissolved (one unit of alpha-glucoside is defined as the amount of enzyme activity to give an absorbance change of 1.0 when assayed at 37° C. and pH 6.80 using the substrate para-nitrophenyl-alpha-D-glucoside). Dilute the solution to 1.00 liter with deionized or distilled water.

EXAMPLE 6

The following procedure can be used to assay for amylases in human serum and urine:
1. Add 1.0 ml of amylase reagent to a cuvet and warm to the reaction temperature of either 30° to 37° C.
2. Add 0.05 ml of sample to the amylase reagent and mix.
3. Determine the change in absorbance per minute at 406 nm during the 4–7 minute interval following sample addition.
4. The units of enzyme activity, expressed as micromoles of para-nitrophenol produced per minute per liter of sample, is calculated by multiplying the change of absorbance per minute by a factor.

The present invention has been described in detail, and examples of the preferred embodiments illustrated herein; however, it will be obvious for a person having ordinary skill in the art to make certain modifications and changes thereof without departing from the spirit and scope of the invention.

I claim:
1. In an enzymatic method for the kinetic analysis of biological fluids in which the hydrolysis of a nitrophenol indicator from its respective substrate is effected at or about neutral pH, the improvement comprising:
    adding to said biological fluid a sensitization effective amount of cyclodextrin so as to effect a hypochromic shift in the wavelength in the unionized homologue of indicator compound thereby increasing the proportion of ionized homologue indicator in said biological fluid; and,
    measuring the level of ionized indicator in the biological fluid at the absorbance maxima of said ionized indicator.

2. In an enzymatic method for the kinetic analysis of biological fluids for alkaline phosphatase in which the hydrolysis of a nitrophenol indicator from its respective substrate is effected at a pH which produces the optimum rate of hydrolysis, the improvement comprising:
    adding to said biological fluid a sensitization effective amount of cyclodextrin so as to effect a shift in the absorbance maxima of the indicator and thereby reduce interference caused by the nitrophenol labeled substrate; and
    measuring the level of indicator in the biological fluid at the absorbance maxima of said indicator.

3. In an enzymatic method for the analysis of biological fluids in which the hydrolysis of a nitrophenol indicator from its respective substrate produces a chromopore which has an absorbance maxima within a range of absorbance of interferring substances also present within said biological fluid, the improvement comprising:
    adding to said biological fluid a sensitization effective amount of cyclodextrin so as to effect a shift in the absorbance maxima of the indicator and thereby reduce the interference caused by other substances within said fluid having appreciable absorbance within the same range of absorbance of the indicator compound prior to shift of its absorbance maxima by said cyclodextrin; and
    measuring the level of indicator in the biological fluid at the absorbance maxima of said indicator.

4. In an enzymatic method for the kinetic analysis of biological fluids for amylase activity in which the enzymatic hydrolysis of a nitrophenol indicator from a nitrophenol oligoglycoside substrate produces a chromophore which can be correlated with the level of amylase activity in said biological fluid, the improvement comprising:
    adding to said biological fluid a sensitization effective amount of cyclodextrin so as to effect an increase in the proportion of chromophore at the optimum pH for the conduct of such analysis; and
    measuring the level of chromophore in the biological fluid at the absorbance maxima of said chromophore advantage.

5. The method of claim 1 wherein the substituted phenol compound is para- or meta-nitrophenol.

6. The method of claim 1 wherein the enzyme assay is for amylase or alpha-glucosidose in biological fluids.

7. The method of claim 1 wherein the concentration of cyclodextrin in the reagent is from about 0.1 to about 100 mg/ml.

8. The method of claim 1 wherein the concentration of cyclodextrin is from about 5 to about 50 mg/ml.

9. The method of claim 6 wherein the pH of the reagent is about 6.6.

10. The method of claim 6 wherein the enzyme assay is for the determination of amylase activity and the reagent further comprises:

para-nitrophenylmaltoheptaoside as a substrate, and maltase.

* * * * *